(12) United States Patent
Jäggi et al.

(10) Patent No.: US 8,702,741 B2
(45) Date of Patent: Apr. 22, 2014

(54) DEVICE FOR INJECTING BONE CEMENT

(75) Inventors: Kurt Jäggi, Bern (CH); Paul Heini, Wabern (CH)

(73) Assignee: DePuy Synthes Products, LLC, Raynham, MA (US)

( * ) Notice: Subject to any disclaimer, the term of this patent is extended or adjusted under 35 U.S.C. 154(b) by 1082 days.

(21) Appl. No.: 11/293,289

(22) Filed: Dec. 1, 2005

(65) Prior Publication Data

US 2006/0085008 A1 Apr. 20, 2006

Related U.S. Application Data

(62) Division of application No. 10/311,978, filed as application No. PCT/CH00/00355 on Jun. 30, 2000, now Pat. No. 6,997,930.

(51) Int. Cl.
*A61B 17/34* (2006.01)

(52) U.S. Cl.
USPC .......................................................... 606/185

(58) Field of Classification Search
USPC .......... 600/184, 567, 566; 604/338, 506, 158, 604/508; 606/92, 94, 95, 304, 167, 170, 606/184, 185
See application file for complete search history.

(56) References Cited

U.S. PATENT DOCUMENTS

| | | | | |
|---|---|---|---|---|
| 4,595,006 A | | 6/1986 | Burke | 128/303 |
| 4,653,489 A | * | 3/1987 | Tronzo | 606/65 |
| 4,681,123 A | * | 7/1987 | Valtchev | 600/566 |
| 4,903,709 A | * | 2/1990 | Skinner | 600/567 |
| 4,909,782 A | * | 3/1990 | Semm et al. | 606/171 |
| 4,969,888 A | | 11/1990 | Scholten et al. | 606/94 |
| 5,031,634 A | * | 7/1991 | Simon | 600/567 |
| 5,080,655 A | | 1/1992 | Haaga | 604/265 |
| 5,098,435 A | * | 3/1992 | Stednitz et al. | 606/916 |
| 5,108,404 A | * | 4/1992 | Scholten et al. | 606/94 |
| 5,287,857 A | * | 2/1994 | Mann | 600/566 |
| 5,331,972 A | * | 7/1994 | Wadhwani et al. | 600/567 |
| 5,357,974 A | * | 10/1994 | Baldridge | 600/567 |

(Continued)

FOREIGN PATENT DOCUMENTS

| | | |
|---|---|---|
| JP | 03-085179 | 4/1991 |
| JP | 04-221538 | 8/1992 |

(Continued)

OTHER PUBLICATIONS

"U.S. Appl. No. 10/311,978, Amendment in Response filed Jun. 8, 2005 to Restriction Requirement mailed May 11, 2005", 4 pgs.

(Continued)

*Primary Examiner* — Thomas McEvoy
(74) *Attorney, Agent, or Firm* — Baker & Hostetler LLP

(57) ABSTRACT

In a device for injecting bone cement, the discharge direction of the bone cement after insertion of the cannula should be controllable in a certain region. This is made possible through a radial exit aperture (5) which is provided on the front end of the cannula (3). Since the cannula is inserted with the aid of a guide wire (1), it has an orifice (4) on its front end, which orifice must be closed off by means of a ball (15) prior to the injection. A plunger serves to insert the ball (15). So that the situation of the radial aperture (5) is known at all times, even with inserted cannula, the handle (17) of the cannula has an asymmetrical shape.

31 Claims, 3 Drawing Sheets

(56) References Cited

U.S. PATENT DOCUMENTS

Figure 2A:
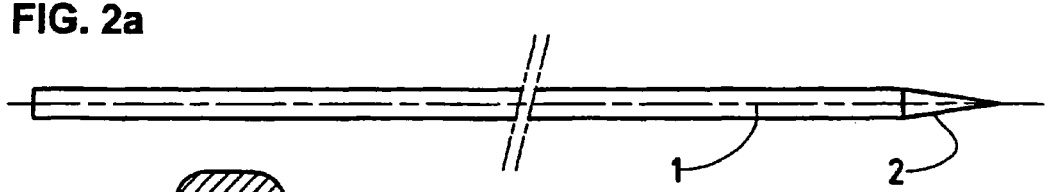
Figure 2B:
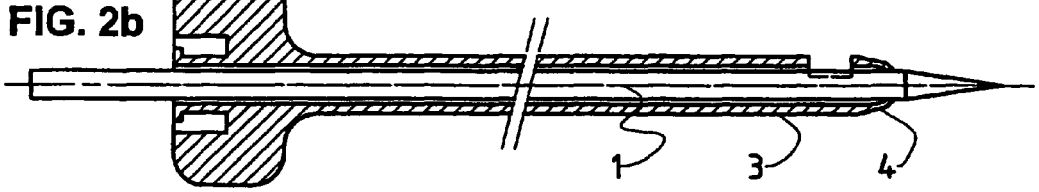
Figure 2C:
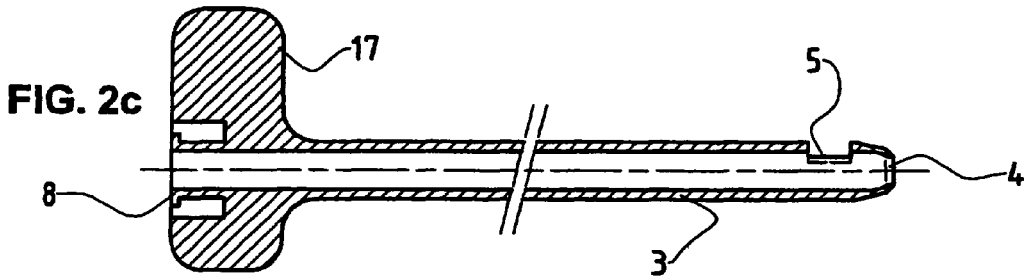

| | | | |
|---|---|---|---|
| 5,360,416 A | | 11/1994 | Ausherman et al. .......... 604/272 |
| 5,458,112 A | * | 10/1995 | Weaver .......................... 600/566 |
| 5,487,392 A | | 1/1996 | Haaga ............................ 123/753 |
| 5,560,373 A | * | 10/1996 | De Santis ....................... 600/566 |
| 5,775,333 A | | 7/1998 | Burbank ........................ 128/754 |
| 5,944,673 A | * | 8/1999 | Gregoire et al. ............... 600/564 |
| 6,019,733 A | * | 2/2000 | Farascioni ..................... 600/564 |
| 6,022,324 A | * | 2/2000 | Skinner ......................... 600/566 |
| 6,264,618 B1 | * | 7/2001 | Landi et al. ................... 600/567 |
| 6,383,190 B1 | | 5/2002 | Preissman | |
| 6,997,930 B1 | | 2/2006 | Jaggi et al. | |
| 2001/0005778 A1 | * | 6/2001 | Ouchi ............................ 600/564 |

FOREIGN PATENT DOCUMENTS

| | | |
|---|---|---|
| JP | 07-313586 | 5/1994 |
| JP | 08-024347 | 1/1996 |
| JP | 09-201330 | 1/1996 |
| WO | WO-9213503 A1 | 8/1992 |
| WO | 9949819 | 10/1999 |
| WO | WO-0009024 A1 | 2/2000 |
| WO | WO-01/32100 A2 | 5/2001 |

OTHER PUBLICATIONS

"U.S. Appl. No. 10/311,978, Notice of Allowance mailed Aug. 24, 2005", 7 pgs.

"U.S. Appl. No. 10/311,978, Preliminary Amendment filed Dec. 23, 2002", 7 pgs.

"U.S. Appl. No. 10/311,978, Restriction Requirement mailed May 11, 2005", 5 pgs.

"European Patent Application No. 04750971.6, Communication mailed Jun. 12, 2008", 5 pgs.

"International Application Serial No. PCT/CH00/00355, International Preliminary Examination Report mailed Jan. 17, 2002", (w/ English Translation),5 pgs.

"International Application Serial No. PCT/CH00/00355, International Search Report mailed May 3, 2001", 2 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11). (1999). 1079-1091.

Stile, R. A., et al., "Synthesis and Characterization of Injectable Poly(N-isopropylacrylamide)-Based Hydrogels That Support Tissue Formation in Vitro", *Macromolecules*, 32 , (1999),7370-7379.

"Japanese Application Serial No. 2002-506661, Questioning document dated Apr. 21, 2010", (w/ English Translation), 9 pgs.

"Canadian Office Action Seriial No. 2,414,351, Amendment filed Aug. 14, 2007 to Office Action mailed Feb. 22, 2007", 8 pgs.

"Canadian Office Action Seriial No. 2,414,351, Office Action mailed Feb. 22, 2007", 2 pgs.

\* cited by examiner

FIG. 1a
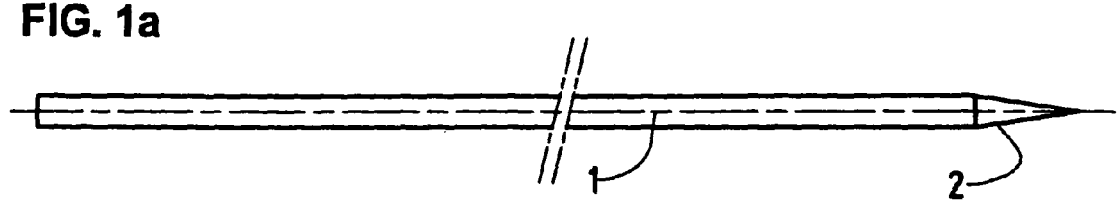
FIG. 1b
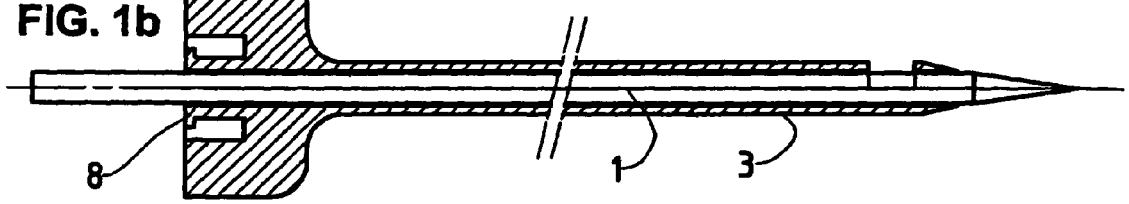
FIG. 1c
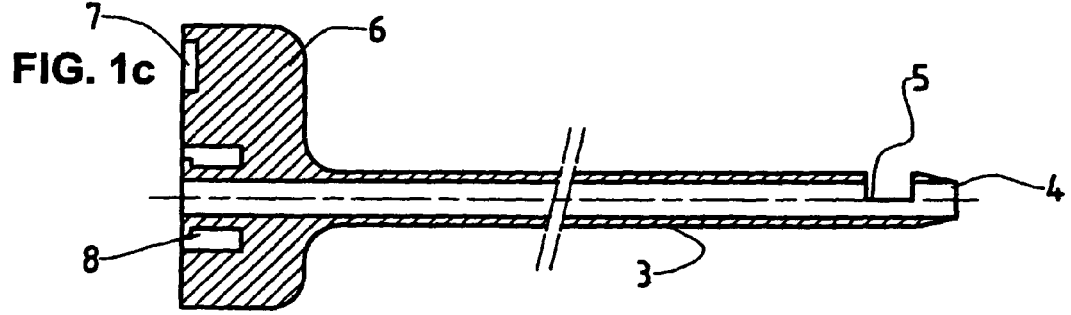
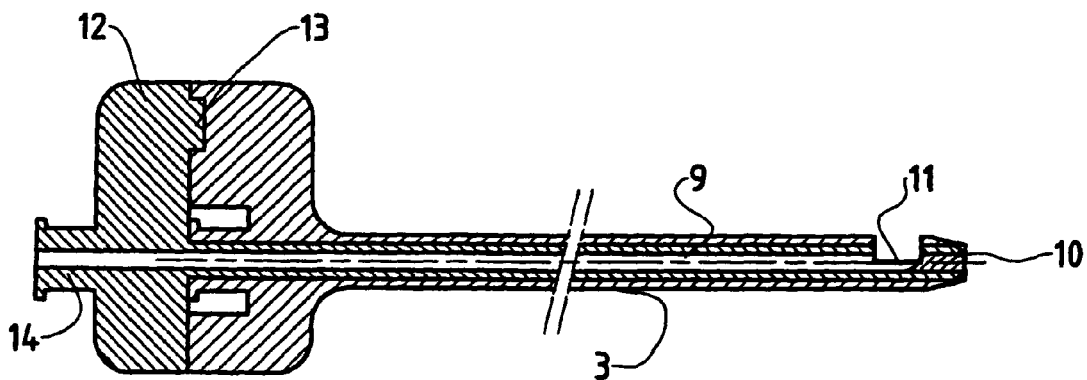
FIG. 1d

FIG. 3a
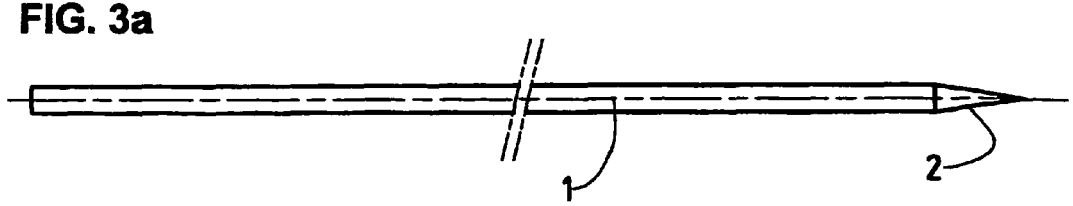
FIG. 3b
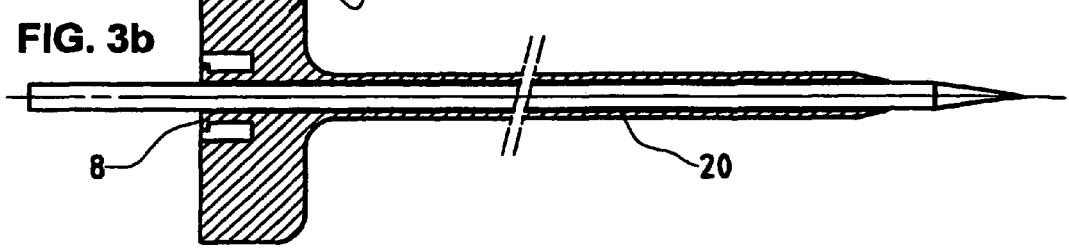
FIG. 3c
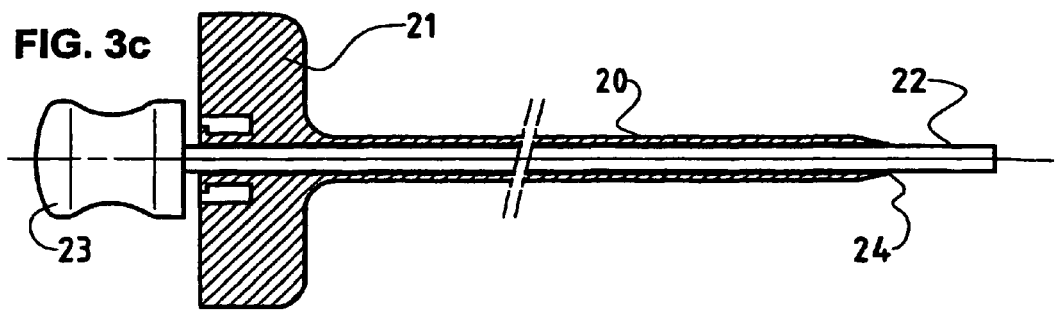
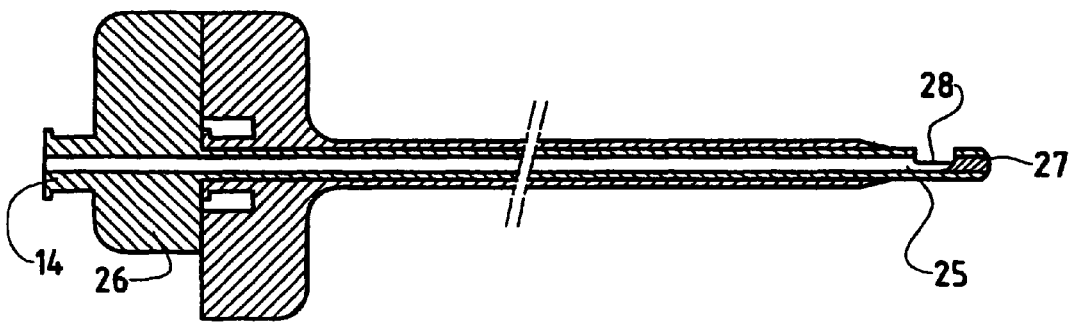
FIG. 3d

DEVICE FOR INJECTING BONE CEMENT

CROSS-REFERENCE TO RELATED APPLICATIONS

This is a divisional of U.S. patent application Ser. No. 10/311,978 filed Dec. 23, 2002, now U.S. Pat. No. 6,997,930 entitled "Device for Injecting Bone Cement," which claims the benefit of priority under 35 U.S.C. 365 to International Application No. PCT/CH00/00355 filed Jun. 30, 2000, both applications which are incorporated herein by reference in their entirety.

The invention relates to a device for injecting bone cement, containing a guide wire and a cannula fitting snugly on the guide wire at least with the inner diameter of its front axial orifice.

Augmenting osteoporotic bones with injected bone cement for fracture prophylaxis is already known. With the injection cannulae used so far with axial exit aperture, the filling cannot be placed with the desired precision in many cases.

It is therefore an object of the invention to propose a device for injecting bone cement in which the discharge direction of the bone cement after insertion of the cannula is able to be guided into a particular area.

According to a first variant of the invention, this object is achieved in that there are closing off means with which the front, axial orifice of the cannula is closable after removal of the guide wire and in that the cannula has a radial aperture, for exit of the bone cement, near the front, axial orifice.

According to a special embodiment of this variant, the closing off means is an inner cannula, closed on its front end, which inner cannula is insertable in the cannula in such a way that its front end closes the orifice of the cannula tightly and has a radial aperture near its front, closed end.

According to another, especially preferred embodiment of the first variant, the diameter of the front, axial orifice of the cannula is smaller than the inner diameter of the cannula and the closing off means is a stopper, the largest diameter of which is larger than the diameter of the front, axial orifice of the cannula. When the orifice is closed off by the stopper, the entire inner cross-section of the cannula is available for the passage of the bone cement so that in this embodiment the flow resistance for the bone cement is considerably less than with the previously mentioned embodiment.

According to a second variant of the invention, this object is achieved in that an inner cannula is provided, closed at its front end, which has near the front, closed end a radial aperture for exit of the bone cement and which fits snugly in the front axial orifice of the cannula at least in a region close to the edge, remote from its front end, of the radial aperture, whereby, after removal of the guide wire, the inner cannula is insertable so far into the cannula that its radial aperture extends beyond the cannula.

Special embodiments of the invention will be explained in the following, by way of example, with reference to the attached drawings.

FIGS. 1a to 1d show a first embodiment example of a device according to the invention with a cannula with radial aperture and an inner cannula, which likewise has a radial aperture, FIGS. 2a to 2f show a second embodiment example of a device according to the invention in which the cannula has a radial aperture and is closed in the front by a body, and FIGS. 3a to 3d show a third embodiment example of a device according to the invention in which the cannula is surpassed in the front by an inner cannula with radial aperture.

FIGS. 1a, 2a and 3a each show a guide wire 1 which is pointed at its front end 2. This front end 2 of the guide wire is driven forward, under X ray control, into the bone up to some millimeters beyond the place at which the bone cement is supposed to be injected. The guide wire typically has a diameter of 2.5 mm and a length of 180 mm; the invention should not be limited, however, to these dimensions.

According to the embodiment example according to FIGS. 1a to 1d, a cannula 3 is pushed over the guide wire. This cannula 3 has at its front end an orifice 4 with a sharply ground circumferential edge whose inner diameter fits snugly over the guide wire. By means of this design, bone tissue is prevented from getting into the interior of the cannula 3 during forwards pushing of the cannula 3. Disposed on the rear (in the drawing left) end of the cannula is a handle 6. The orifice 4 of the cannula can be slightly reduced and the remaining inner diameter of the cannula can be 3.1 mm, for example. The outer diameter of the cannula 3 can be 4 mm, for instance, and its length up to the handle 130 mm. Disposed in the cannula near the orifice 4 is a radial aperture 5, the width of which is somewhat smaller than the inner diameter of the cannula. The length of this radial aperture 5 is at least the same as that of the aperture of the inner cannula 9 described further below. The handle is of asymmetrical shape, for instance with a pointer-like form the tip of which is aligned with the radial aperture 5, so that the surgeon knows the angular position of the radial opening 5 at all times. The handle 6 has moreover a recess 7 and a coupling 8, the function of which will be explained further below. FIG. 1c shows the cannula after the guide wire 1 has been pulled out.

An inner cannula 9 is inserted in the cannula 3 in FIG. 1d. The outer diameter of this inner cannula is 3.0 mm, for instance, so that it can be pushed with play in the cannula 3. The inner diameter of the inner cannula can be 2.5 mm, for example. The front end 10 of the inner cannula is closed, and the length of the inner cannula 9 as well as the outer diameter of the end 10 are dimensioned such that, with completely inserted inner cannula 9, the orifice 4 of the cannula 3 is tightly sealed off. Located on the rear end of the inner cannula 9 is a handle 12, which is also of asymmetrical design, like the handle 6 of the cannula 3. The handle 12 has a protrusion 13, which forms together with the recess 7 provided on the handle 6 a snap in locking device. Furthermore the inner cannula 9 has a radial aperture 11 in the vicinity of the end 10, which radial aperture coincides with the aperture 5 of the cannula, with the snap in locking device 7, 13 in snapped-in state. The width of the radial aperture 11 of the inner cannula is somewhat less than its inner diameter, and the length of the aperture 11 is dimensioned in such a way that the exit cross-section of the aperture is at least just as large as the inner cross-section of the inner cannula 9. A coupling 14 provided on the handle 12 serves for attachment of a bone cement source, for instance a needle.

A bone cement injection with this first embodiment of the device according to the invention runs as follows. First, the guide wire 1 is driven in, as mentioned above. Then the cannula 3 is pushed over the guide wire 1 and pressed in until its radial aperture 5 sits at the place where the injection is supposed to take place. Now the guide wire 1 is pulled out and the inner cannula 9 is inserted in the cannula 3. After the two handles 6 and 12 are locked together by means of the snap in locking device and a needle with bone cement is connected with the coupling 14, the injection can begin. Thanks to the inventive design of the device, the physician is able to control the discharge direction of the bone cement into an area-even during the injection by turning the two handles 6 and 12, locked together, and thus also the two radial apertures 5 and 11, aligned with one another.

Figure 2D:
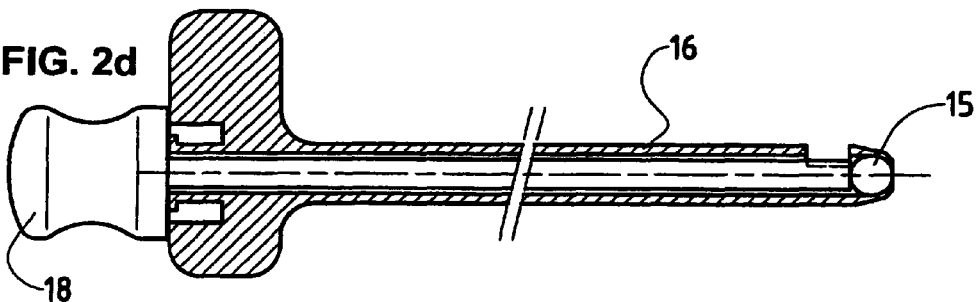
Figure 2E:
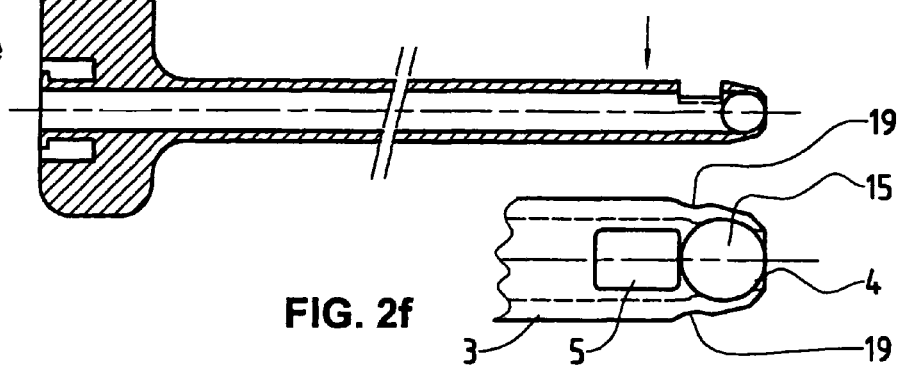
Figure 2F:
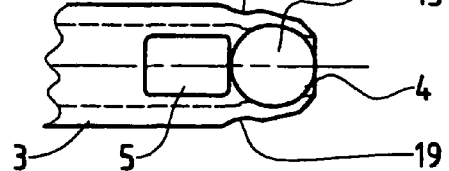

FIGS. 2*a* to 2*f* show a second embodiment of the device according to the invention, a guide wire 1 with a tip 2 being shown once again n FIG. 2*a*. The cannula 3 has in principle the same construction as that in the first embodiment example described above, which is why the same reference numerals have been used here. One difference is that with the cannula according to FIGS. 2*b* to 2*e*, the handle 17 is shaped differently from the handle 7 according to FIGS. 1*b* to 1*d*, and in particular has no recess 7 because in this second embodiment example there is no inner cannula 9. The orifice 4 of the cannula 3 is closed off with a ball 15 in this embodiment, which ball is pushed into its place with a plunger 16, as is shown in FIG. 2*d*, after pulling back of the guide wire 1. The plunger 16 has a support 18 and is so long that the ball 15 sits at the right place when the support 18 abuts the handle 17 of the cannula 3. In this embodiment example it is necessary for the orifice 4 of the cannula to be slightly reduced. The diameter of the ball 15 is slightly smaller than the inner diameter of the cannula 3, but somewhat larger than the inner diameter of the orifice 4 and also larger than the width of the radial aperture 5. In this way it is ensured that the ball 15 can be easily inserted into the cannula 3, but cannot escape through the radial aperture 5 or the orifice 4. So that the ball 15 does not roll back in an undesired way after it has been pushed in its place by the plunger 16, small indentations 19 are provided in the walling of the cannula 3, as is to be seen in FIG. 2*f*. The indentations are dimensioned in such a way that during pushing in of the ball 15 a certain resistance must be overcome.

This second embodiment type of the device according to the invention has the big advantage over the other embodiment types that no inner cannula is necessary and thus the entire inner cross-section of the cannula 3 is available for the flow of the bone cement. This results in a considerably lower pressure loss during injecting.

In the third embodiment example illustrated in FIGS. 3*a* to 3*d* a guide wire is likewise provided, as can be seen from FIG. 3*a*. The cannula here has the reference numeral 20, and differs from the previously described cannulae in that it has no radial aperture. Thus the handle 21 of the cannula 20 is also not asymmetrical. FIG. 3*c* shows an obturator 22 with which the physician makes space outside the orifice 24 of the cannula 20 after the insertion of the cannula 20 in order to then be able to insert the inner cannula 25, as is shown in FIG. 3*d*. The obturator 22 has a head 23 and its length is dimensioned such that when the head 23 abuts the handle 21 of the cannula, its front end projects so far out of the orifice 24 as the inner cannula 25 does later. The inner cannula 25 has a radial aperture 28, near its closed end 27, for exit of the bone cement. At the other end the inner cannula 25 has a handle 26 which is designed asymmetrically such that the situation of the radial aperture 28 can be seen from its position.

With this third embodiment of the invention a bone cement injection runs at the beginning the same way as with both other embodiments in that first the guide wire 1 is driven in and then the cannula 20 is pushed over the guide wire 1. After removal of the guide wire 1, the bone tissue is pushed back and compressed with the obturator 22 in the region of the orifice 24 so far that then the inner cannula 25 can be inserted without too much resistance. After insertion of the inner cannula 20 <sic. 25>, its radial aperture is aligned as desired through turning of the handle 26, and the bone cement is injected with a needle connected by means of the coupling 14.

All three embodiments described of the device according to the invention thus allow an exact placement of the bone cement filling in that the discharge direction of the bone cement can be determined by turning the respective cannula and can even be changed during the injection.

So that both the cannula 3 according to the first embodiment example and the cannula 20 according to the third embodiment example can also be used for axial injection of bone cement, their handles 6 and 21 have a coupling 8 for direct attachment of a needle. The range of cannulae is thereby kept small.

The invention claimed is:

1. An injection device configured to inject a flowable substance into bone, the injection device comprising:
    an outer cannula including an outer cannula handle and an axial orifice opposite the outer cannula handle, the outer cannula handle including a proximal handle end and an opposed front handle end;
    an inner cannula insertable into the outer cannula, the inner cannula defining a proximal end and a front end spaced from the proximal end along an axial direction, the inner cannula further including an inner cannula wall that extends between the proximal end and the front end so as to define an inner axial passageway that extends from the proximal end to the front end along the axial direction, the inner cannula defining a radial aperture having an aperture distal end that extends through the inner cannula wall along a radial direction that is perpendicular to the axial direction, the proximal end of the inner cannula including an inner cannula handle, the inner cannula handle having a proximal handle end and a front handle end spaced from the proximal handle end along the axial direction,
    wherein 1) the front end defines a curved surface that closes the axial passageway, the curved surface being curved as it extends along the radial direction so as to guide the flowable substance flowing in the inner axial passageway to exit the cannula through the radial aperture, and 2) the curved surface is disposed beyond the axial orifice of the outer cannula when A) the inner cannula is inserted in the outer cannula, and B) the front handle end of the inner cannula handle abuts the proximal handle end of the outer cannula handle; and
    an obturator sized and configured to removeably slide into the outer cannula.

2. The injection device of claim 1, wherein the radial aperture is located proximate the closed front end of the inner cannula.

3. The injection device of claim 1, wherein the inner cannula is rotatable with respect to and inside the outer cannula to change the angular orientation of the radial aperture.

4. The injection device of claim 1, wherein the radial aperture has a rectilinear shape.

5. The injection device of claim 1, wherein the device further comprises a guide wire sized and configured to penetrate the bone, and the outer cannula being slidable along the guide wire so as to engage with the bone.

6. The injection device of claim 1, wherein the inner cannula handle includes an asymmetrically-shaped handle body.

7. The injection device of claim 6, wherein the asymmetrical handle body has an enlarged portion that extends along the radial direction and is circumferentially aligned with the radial aperture so that the enlarged portion and the radial aperture have approximately the same angular position on the inner cannula.

8. The injection device of claim 1, wherein the flowable substance is bone cement.

9. The injection device of claim 1, wherein the radial aperture defines an aperture proximal end and an aperture distal end spaced from the aperture proximal end along the axial direction toward the inner cannula front end, and the curved surface extends from the aperture distal end.

10. The injection device of claim 1, wherein the radial aperture is free of obstructions to facilitate ejection of the flowable substance from the inner axial passageway through the radial aperture.

11. An injection device configured to inject bone cement into bone, the injection device comprising:
    an outer cannula including an outer cannula handle and an axial orifice opposite the outer cannula handle, the outer cannula handle including a proximal handle end and an opposed distal handle end;
    an inner cannula sized to be received in the outer cannula, the inner cannula defining a proximal end, a closed distal end spaced from the proximal end along an axial direction, and an inner cannula wall that defines an inner axial passageway that extends between the proximal end and the closed distal end along the axial direction,
    wherein 1) the inner cannula defines a radial aperture that extends through the inner cannula wall along a radial direction that is perpendicular to the axial direction, the radial aperture defining an aperture proximal end and an aperture distal end that is spaced from the aperture proximal end along the axial direction, the radial aperture having a length that extends from the aperture proximal end to the aperture distal end and does not increase as the aperture extends along the radial direction away from the inner axial passageway, 2) the closed distal end is configured to direct the bone cement traveling in the inner axial passageway out the radial aperture, and 3) the proximal end includes an inner cannula handle having a proximal handle end and a distal handle end spaced from the proximal handle end along the axial direction,
    wherein the radial aperture is disposed beyond the axial orifice when the inner cannula is received in the outer cannula and the distal handle end of the inner cannula handle abuts the proximal handle end of the outer cannula handle; and
    an obturator sized and configured to removeably slide into the outer cannula.

12. The injection device of claim 11, wherein the inner cannula handle includes an asymmetrically-shaped handle body.

13. The injection device of claim 12, wherein when the injection device is inserted into the bone, the inner cannula is rotatable with respect to the outer cannula to change the angular orientation of the radial aperture as the bone cement is being ejected from the radial aperture along the radial direction into the bone.

14. The injection device of claim 11, wherein the radial aperture has a rectilinear shape.

15. The injection device of claim 11, wherein the inner axial passageway of the inner cannula terminates with a coupling at the proximal end of the inner cannula for connecting to a syringe.

16. The injection device of claim 11, further comprising a coupling at the proximal end of the outer cannula for connecting to a syringe.

17. The injection device of claim 11, wherein the length of the radial aperture is substantially constant along the radial direction.

18. An injection kit configured to inject a flowable substance into a bone, the kit comprising:
    an outer cannula defining a length and a first inner axial passageway, the outer cannula including an axial orifice at a front end and an outer cannula handle at a proximal end;
    an inner cannula sized and configured to be engageably detachable from the outer cannula, the inner cannula including a proximal end, a closed front end spaced from the proximal end along an axial direction, and a second inner axial passageway that extends along the axial direction, and an inner cannula handle at the proximal end of the inner cannula, the second inner axial passageway having a width, the inner cannula extending through and beyond the front end of the outer cannula when the inner and outer cannulas are engaged, wherein engagement of the inner and outer cannulas includes the inner cannula handle configured for abutting the outer cannula handle,
    the inner cannula including a radial aperture disposed in a portion of the inner cannula that extends beyond the front end of the outer cannula when the inner cannula is engaged with the outer cannula, the radial aperture extends along a radial direction that is perpendicular to the axial direction, the radial aperture communicating with the second inner passageway, the inner cannula further including an injector coupling at the proximal end of the inner cannula;
    a guide wire sized and configured to be removably inserted into the first inner axial passageway of the outer cannula, the guide wire extending beyond the front end of the outer cannula when inserted therein;
    an obturator sized and configured to be removably inserted into the first inner axial passageway of the outer cannula, the obturator extending beyond the front end of the outer cannula when inserted therein;
    whereby the inner cannula, guide wire, and obturator are configured to be interchangeably inserted into the outer cannula during a surgical procedure; and
    a flowable substance injector removably attachable to the injector coupling;
    wherein a proximal surface of the closed front end of the inner cannula includes a rounded transition extending proximally from a distal end of the radial aperture and across the width of the second inner axial passageway, the rounded transition configured to direct the flowable substance from traveling in the axial direction along the second inner axial passageway to traveling in the radial direction out of the radial aperture.

19. The injection kit of claim 18, wherein the inner cannula is rotatable inside the outer cannula.

20. The injection kit of claim 18, wherein the inner cannula handle includes an asymmetrical handle body.

21. The injection kit of claim 18, further comprising the flowable substance.

22. The injection kit of claim 21, wherein the flowable substance is bone cement.

23. An injection device configured to inject a flowable substance into a bone, the injection device comprising:
    an outer cannula including an outer cannula handle and an axial orifice opposite the outer cannula handle, the outer cannula having a proximal handle end and an opposed front handle end;
    an inner cannula insertable into the outer cannula, the inner cannula defining a proximal end and a front end spaced from the proximal end along an axial direction, the inner cannula further including an inner cannula wall that extends between the proximal end and the front end so as to define an inner axial passageway that extends from the proximal end to the front end along the axial direction, the inner cannula defining a radial aperture having an aperture distal end that extends through the inner cannula wall along a radial direction that is perpendicular to the axial direction, the proximal end including an inner cannula handle, the inner cannula handle having a proximal handle end and an opposed distal handle end, wherein 1) the front end defines a guide surface that closes the inner axial passageway, the guide surface defining two locations that are spaced from each other along both the radial direction and the axial direction, such that the guide surface is configured to guide the flowable substance flowing in the inner axial passageway to exit the inner cannula through the radial aperture, and 2) the guide surface is disposed beyond the axial orifice of the outer cannula when the inner cannula is inserted in the outer cannula and the distal handle end of the inner cannula handle abuts the proximal handle end of the outer cannula handle; and an obturator sized and configured to removeably slide into the outer cannula.

24. The injection device of claim 23, the outer cannula handle defines an outer axial passageway that extends from the proximal handle end of the outer cannula to the axial orifice, the outer axial passageway sized to receive either the obturator or the inner cannula.

25. The injection device of claim 24, wherein at least a portion of the radial aperture extends beyond the front end of the outer cannula when the inner cannula is engaged with the outer cannula.

26. The injection device of claim 23, wherein the outer cannula handle includes a first coupling configured to attach to a source of the flowable material and the inner cannula handle includes a second coupling configured to attach to a source of the flowable material.

27. The injection device of claim 26, wherein the first coupling and the second coupling are axially aligned with the inner axial passageway when the outer cannula and the inner cannula are engaged.

28. The injection device of claim 27, wherein engagement of the inner cannula and the outer cannula includes abutment of the inner cannula handle with the first coupling.

29. The injection device of claim 27, wherein the first coupling is configured and dimensioned to receive the inner cannula therethrough.

30. The injection device of claim 23, wherein each of the two locations is aligned with the inner axial passageway along the axial direction.

31. The injection device of claim 23, wherein the radial aperture is free of obstructions to facilitate ejection of the flowable substance from the inner axial passageway through the radial aperture.

* * * * *